United States Patent [19]

Bredeweg et al.

[11] Patent Number: 4,760,732

[45] Date of Patent: Aug. 2, 1988

[54] FLOW PROGRAMMER FOR GAS CHROMATOGRAPHY

[75] Inventors: Robert A. Bredeweg; Jeffrey R. Larson; Stephen W. Barr, all of Midland, Mich.

[73] Assignee: The Dow Chemical Company, Midland, Mich.

[21] Appl. No.: 67,836

[22] Filed: Jun. 29, 1987

[51] Int. Cl.$^4$ ............................................. G01N 30/32
[52] U.S. Cl. ....................................................... 73/23.1
[58] Field of Search ........................................ 73/23.1

[56] References Cited

U.S. PATENT DOCUMENTS

| | | | |
|---|---|---|---|
| 3,299,693 | 1/1967 | Kieselbach | 73/23.1 |
| 3,879,984 | 4/1975 | Welland | 73/23.1 |
| 4,373,549 | 2/1983 | Nalepa et al. | 73/23.1 X |

OTHER PUBLICATIONS

Lee, Milton L. et al., "Open Tubular Column Gas Chromatography, Theory and Practice," A Wiley-Interscience Publication, pp. 195–198 and 227.
Nygren, Soren et al., "Flow Programming in Glass Capillary Column-Electron Capture Gas Chromatography by Using the Valve in the Splitter Line," J. of Chromatography, 123, (1976), 101–102, 107–108.
Nygren, Soren, "Exponential Flow Programming in Gas Chromatography," J. of Chromatography, 142, (1977), 109–116.
Nohl, A., "Flow Programming of Short Capillary Columns," Chromatography Review, vol. 11, No. 3, (10/1984), 10–11.
DoDo, Gerald H., "Optimized Flow Programming for Temperature-Programmed Gas Chromatography," J. of Chromatography, 328, (1985), 49–53.
Nygren, Soren, "Applications of a Computerized Flow Programmer for Capillary Column Gas Chromatography," Anal. Chem., (1985), 57, 2748–2751.
"User's Manual for Porter Thermal Mass Flowmeter and Thermal Mass Flow Controller," Model: 201-SSVB, Ser. No.: 8603193, Porter Inst. Co., Inc.

Primary Examiner—John Chapman
Assistant Examiner—Joseph W. Roskos
Attorney, Agent, or Firm—Timothy S. Stevens

[57] ABSTRACT

A flow programmer for gas chromatography of the type having a mass flow meter for controlling the flow rate of a gas chromatography carrier gas controllable at a selected carrier gas flow rate program by an electrical input to the mass flow meter and an electrical circuit for generating the electrical input. The improvement is that the electrical circuit for generating the electrical input is an analog electrical circuit which includes an operational amplifier having an electrical capacitor in the feedback loop of the operational amplifier to produce a selected voltage input program.

1 Claim, 1 Drawing Sheet

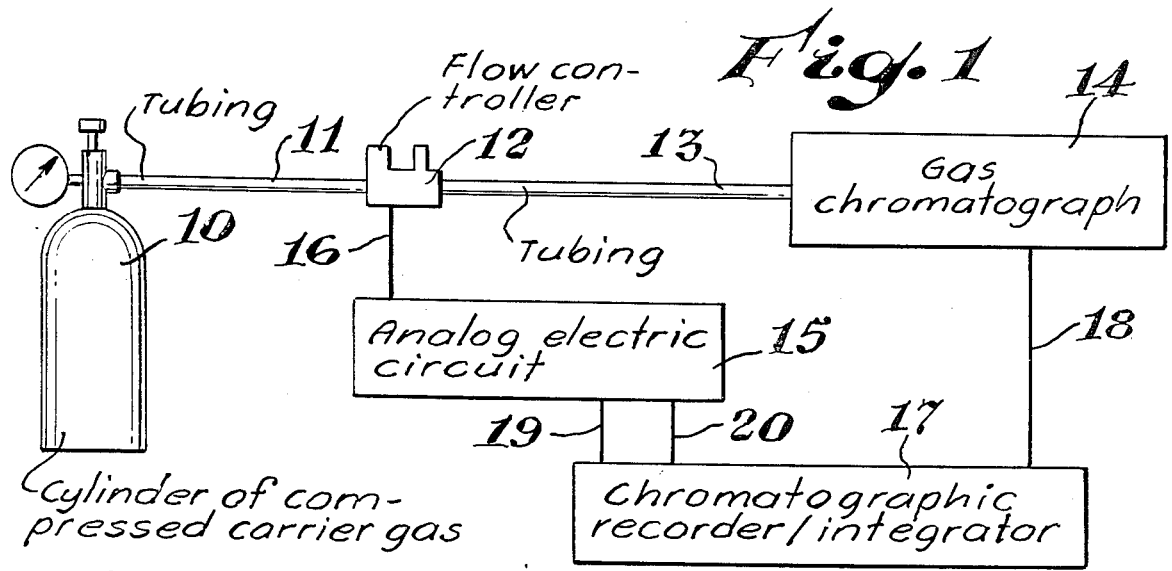
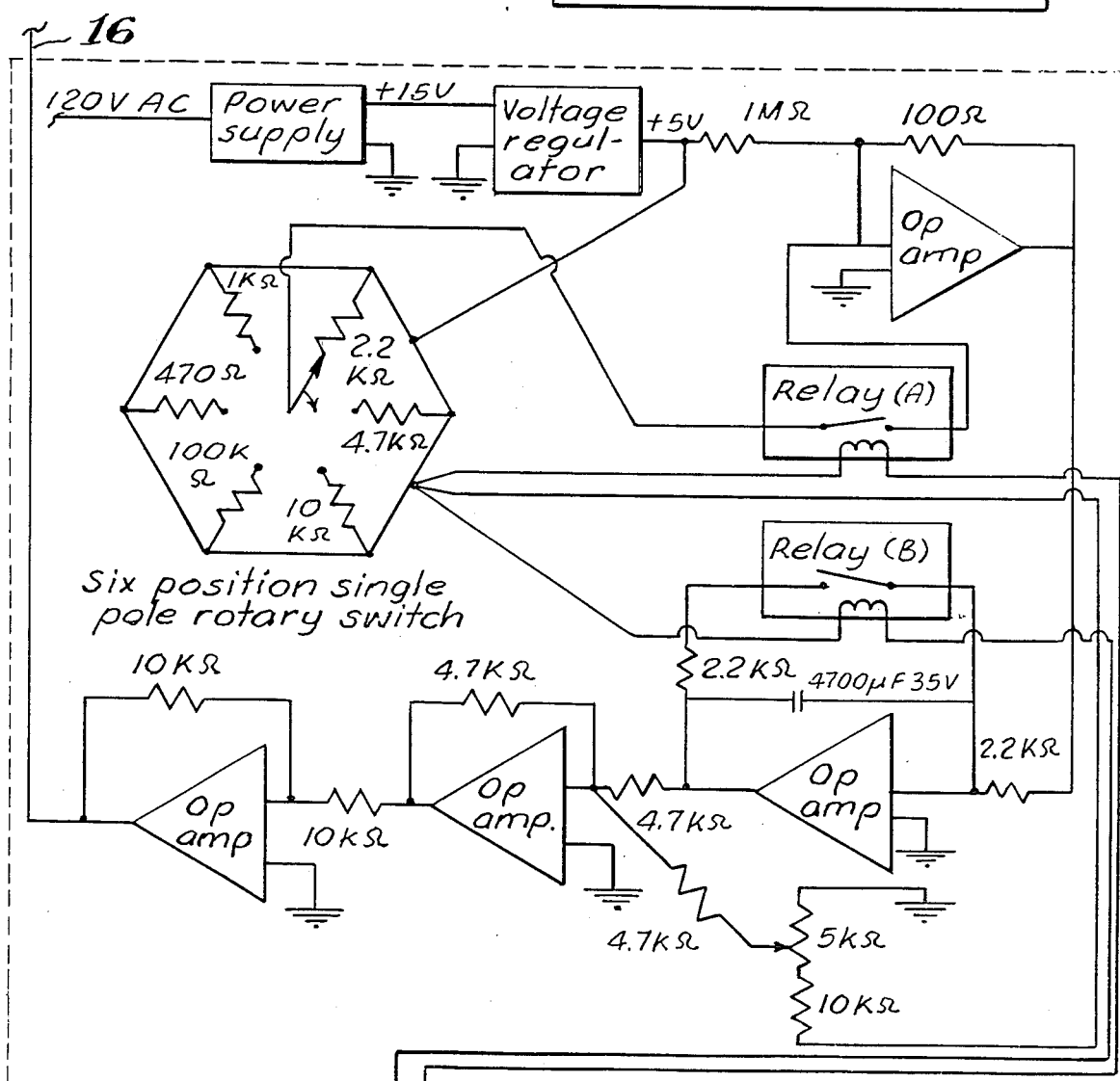

FLOW PROGRAMMER FOR GAS CHROMATOGRAPHY

FIELD OF THE INVENTION

The invention is in the field of gas chromatography and more specifically in the field of flow programmed gas chromatography.

BACKGROUND OF THE INVENTION

Milton Lee, et al, in the book entitled Open Tubular Column Gas Chromatography stated on page 195, "Carrier gas flow programming is a technique that allows the carrier gas flow rate in the column to be gradually increased to reduce the analysis time and to increase the detectability of highly retained samples. It has the following advantages over constant flow GC: (a) It allows rapid elution of compounds with high boiling points at relatively low column temperatures. (b) It allows better baseline stability and extends column lifetime in comparison to temperature programming. The evaporation rate of the stationary liquid phase changes linearly with flow rate and exponentially with temperature. (c) Low-temperature GC is particularly favorable for the analysis of thermally labile compounds. (d) It is particularly favorable for open tubular column GC because the H vs. u plot is relatively flat. (e) It demands no special apparatus. It can be effectively applied with adjustment of the column inlet pressure. (f) The initial carrier gas flow rate can be restored very rapidly and, thus more chromatographic runs can be made in a given time."

Known apparatus for carrier gas flow programming includes the suggestion of Nygren et al in the Journal of Chromatography, 1976, Volume 123, pages 101–108 to use a stepper motor, controlled by an electronic programming unit, to rotate the valve stem of a metering valve in the side outlet of an inlet splitter of a split type capillary GC system. In 1977 Nygren et al, in the Journal of Chromatography, Volume 142, pages 109–116, described two different electronic programming units comprising digital electronic circuits. Nohl, in Chromatography Review, 1984, Volume 11, Number 3, pages 10 and 11, described a multiple chamber/solenoid valve system in the side outlet of an inlet splitter of a split type capillary GC system. Dodo et al, in The Journal of Chromatography, 1985, Volume 328, pages 49–53, described a flow controller comprising a digital electronic circuit. Nygren et al, in Analytical Chemistry, 1985, pages 2748–2751 also described a flow controller comprising a digital electronic circuit. These digital electronic based systems have proven to be workable in flow programmed GC but are relatively expensive and especially so in low volume production. Analog electronic circuits are known to generate continuously increasing voltage outputs comprising an electrical capacitor in the feedback loop of an operational amplifier. Flow controllers are known for constant flow GC wherein the constant flow rate of the carrier gas is selected by inputting to the flow controller a constant voltage signal, e.g., the Porter Model 201-SSVB flow controller, Porter Instrument Company, Inc., Hatfield, Pa., as described in the Porter publication FM-300, dated Sept. 1985, entitled Users Manual For Porter Thermal Mass Flowmeter and Thermal Mass Flow Controller, herein fully incorporated by reference.

SUMMARY OF THE INVENTION

The invention is an improved flow programmer for gas chromatography of the type having: (a) a means for controlling the flow rate of a gas chromatography carrier gas controllable at a selected carrier gas flow rate program by an electrical input thereto; and (b) a means for generating the electrical input. The improvement comprises that the means for generating the electrical input consists essentially of an analog electrical circuit which produces a selected voltage input program. Preferably, the means for controlling the flow rate of a gas chromatography carrier gas comprises a mass flow meter. Preferably, the analog electrical circuit comprises at least one operational amplifier and at least one electrical capacitor.

BRIEF DESCRIPTION OF THE DRAWINGS

FIG. 1 is a block diagram of a gas chromatography system incorporating the improved flow programmer of the present invention.

FIG. 2 is an electrical circuit diagram of an analog electrical circuit for generating a voltage program of the present invention.

DETAILED DESCRIPTION OF THE INVENTION

Referring to FIG. 1, therein is shown a block diagram of a typical example of a gas chromatography system incorporating the improved flow programmer of the present invention. The system includes a cylinder of compressed carrier gas 10. A length of tubing 11 conducts the carrier gas to a flow controller 12. A length of tubing 13 then conducts the carrier gas to a gas chromatograph 14. The flow controller 12 receives a voltage input from an analog electrical circuit 15 by way of a wire 16. The gas chromatograph 14 produces an output signal that is sent to a chromatographic recorder/integrator 17 by way of a wire 18. The analog electrical circuit 15 produces a reproducible continuously varying voltage signal generally of increasing voltage as a function of time, i.e., a voltage program. The flow controller 12, the gas chromatograph 14, the analog electrical circuit 15 and the chromatographic recorder/integrator 17 are all electrically grounded.

Referring to FIG. 2, therein is shown a circuit diagram of a highly preferred analog electrical circuit 15 of the present invention. The circuit shown in FIG. 2 is but one example of the almost unlimited variety of analog electrical circuits that could be devised for generating a voltage program.

Referring again to FIG. 1, the flow controller 12 incorporates a means for varying the flow rate of the carrier gas as a function of the varying voltage input from the analog electrical circuit 15. Preferably, the flow controller 12 incorporates a means of measuring the flow rate of the carrier gas and thereby accurately controlling the flow rate of carrier gas as a function of input voltage despite any variation in the back pressure of carrier gas in the tubing 13. Such a preferred flow controller 12 is the Porter flow controller Model 201-SSVB available from the Porter Instrument Company, Hatfield, Pa. 19440. However, the flow controller 12 can simply, for example, be a needle valve/solenoid combination where the position of the valve stem is determined by the voltage input to the solenoid. Alternatively, the flow controller 12 can be an electronic pressure regulator such as the Eurotherm Model 821 available from Eurotherm Limited, England. Preferably, the program of the analog electrical circuit 15 is automatically initiated at the beginning of the chromatogram by interfacing the chromatographic recorder/integrator 17 with the analog electrical circuit 15 by way of wires 19 and 20. Most gas chromatographs have carrier gas flow control systems and for use in this invention these systems are bypassed or more preferably, when possible, adjusted for very high flow so that control of the flow rate of the carrier gas is by the flow controller 12.

EXAMPLE 1

The analog electrical circuit 15, shown in FIG. 2, is assembled using a Sola Electric 84-15-2135 power supply, a Radio Shack 7815 voltage regulator, Newark Electric JWD107-1 normally open reed relays, a Radio Shack 324 quad operational amplifier, and the other components as shown. The wire 16 is connected to the "set point in" terminal of a Porter Model 201-SSVB flow controller, supra. The flow controller is powered by the power supply shown in FIG. 2. A digital volt meter is connected to terminals 2 and 3 of the flow controller (not shown) as an indicator of carrier gas flow rate. A cylinder of GC carrier gas grade helium is connected to the inlet of the flow controller (at a regulated pressure of about 80 psig) and the outlet of the flow controller is connected directly to the injection port, a Varian 3700 GC equipped with a flame ionization detector (FID). A 15 meter long, 0.53 millimeter internal diameter, 1 micron thick film OV1701 capillary column is installed in the GC. The oven temperature of the GC is set at 150 degrees centigrade. The FID is connected to the detector input terminal of a Spectra-Physics Model 4100 chromatographic recorder/integrator. Wire 19 is connected to the T3 timed relay terminal of the recorder/integrator. Wire 20 is connected to the T4 timed relay terminal of the recorder/integrator. The recorder integrator is programmed so that at the beginning of a chromatographic run (initiated by pressing the "inject" button of the recorder/integrator coincident with the injection of a sample into the injection port of the GC) the timed relay T3 of the recorder/integrator opens, thereby opening relay (b) of FIG. 2, and at 3 minutes after the "inject" button is pushed, the timed relay T4 of the recorder/integrator closes, thereby closing relay (a) of FIG. 2. The opening of relay (b) and the subsequent closing of relay (a) initiates a continuously rising voltage program. The initial voltage of the program is determined by the setting of the 5K potentiometer of FIG. 2, and the potentiometer is set so that the initial carrier gas flow rate is 3 cc/min.

The rate of voltage rise with time is determined by the position of the six position switch of FIG. 2, and results in a carrier gas flow rate ramp of from about 0.2 to about 50 cc/min/min. The six position switch is set at position 3 which results in a flow rate ramp of about 6 cc/min/min. At the end of the chromatographic run the timed relay T3 closes and the timed relay T4 opens, thereby returning the voltage program to the initial voltage (and in about 45 seconds, the carrier gas flow rate returns to the flow rate corresponding to the initial voltage of the voltage program). This example teaches how to make a preferred embodiment of the present invention.

EXAMPLE 2

A 0.2 microliter on-column injection of hexane containing C13, C14, C15, C16, C17, and C19 alkyl hydrocarbons is made using the system of Example 1, and the inject button is pushed on the recorder/integrator. The C13 peak elutes at about 3 minutes and the C19 peak elutes at about 7.7 minutes with the other peaks spaced progressively between these two. This example teaches how to use the present invention.

COMPARATIVE EXAMPLE

A 0.2 microliter on-column injection of the sample of Example 2 is made using the system of Example 1 without initiating flow programming, i.e., at a constant 3 cc/min carrier gas flow rate, resulting in elution of the C13 peak at about 3 minutes, elution of the C17 peak at about 13 minutes, and no elution of the C19 peak within 25 minutes. The C17 peak eluting at about 13 minutes is about 6 times shorter than the C17 peak eluting at about 6.3 minutes of Example 2. This comparative example shows the advantage of flow programming in reducing elution time and increasing sensitivity of analysis for the higher molecular weight sample components.

What is claimed is:

1. In an improved flow programmer for gas chromatography comprising means for controlling the flow rate of a gas chromatography carrier gas controllable at a selected carrier gas flow rate program by an electrical input thereto and a means for generating the electrical input, the means for controlling the flow rate of a gas chromatography carrier gas incorporating a mass flow meter, wherein the improvement comprises:

that the means for generating the electrical input consists essentially of an analog electrical circuit which produces a selected voltage input program, the circuit comprising at least one operational amplifier and at least one electrical capacitor.

* * * * *

UNITED STATES PATENT AND TRADEMARK OFFICE
CERTIFICATE OF CORRECTION

PATENT NO. : 4,760,732

DATED : Aug. 2, 1988

INVENTOR(S) : Robert A. Bredeweg; Jeffrey R. Larson; Stephen W. Barr

It is certified that error appears in the above-identified patent and that said Letters Patent is hereby corrected as shown below:

Col. 1, line 37, delete "oontrolled" and insert --controlled--.

Col. 1, line 50, delete "oircuit" and insert --circuit--.

Col. 2, line 11, delete "produoes" and insert --produces--.

Signed and Sealed this

Fifteenth Day of August, 1989

Attest:

DONALD J. QUIGG

Attesting Officer

Commissioner of Patents and Trademarks